United States Patent [19]

Lanzara et al.

[11] Patent Number: 5,712,889
[45] Date of Patent: Jan. 27, 1998

[54] SCANNED VOLUME CT SCANNER

[76] Inventors: Giovanni Lanzara, Largo Dell'Olglata, Isola 61/A, 00123 Rome, Italy; Douglas Perry Boyd, 1115 Lakeview Dr., Hillsborough, Calif. 94010

[21] Appl. No.: 827,781

[22] Filed: Apr. 11, 1997

Related U.S. Application Data

[63] Continuation of Ser. No. 675,420, Jul. 3, 1996, abandoned, which is a continuation of Ser. No. 294,964, Aug. 24, 1994, abandoned.

[51] Int. Cl.[6] ................................ G01N 23/00
[52] U.S. Cl. ..................... 378/19; 378/4; 378/113; 378/137
[58] Field of Search ................. 378/19, 4, 113, 378/137

[56] References Cited

U.S. PATENT DOCUMENTS

| | | |
|---|---|---|
| 4,002,917 | 1/1977 | Mayo .................................. 378/14 |
| 4,250,425 | 2/1981 | Gabbay et al. ..................... 378/137 |
| 4,352,021 | 9/1982 | Boyd et al. . |
| 4,521,901 | 6/1985 | Rand . |
| 4,531,226 | 7/1985 | Peschmann . |
| 4,535,243 | 8/1985 | Peschmann . |
| 4,621,213 | 11/1986 | Rand . |
| 4,644,168 | 2/1987 | Rand et al. . |
| 4,944,448 | 7/1990 | Peschmann et al. . |
| 5,182,764 | 1/1993 | Peschmann et al. . |
| 5,228,069 | 7/1993 | Arenson et al. ..................... 378/4 |
| 5,400,379 | 3/1995 | Pfoh et al. ........................ 378/19 |

FOREIGN PATENT DOCUMENTS 1528574  10/1978  United Kingdom ............ 378/19

*Primary Examiner*—Craig E. Church
*Attorney, Agent, or Firm*—Flehr, Hohbach, Test, Albritton & Herbert, LLP

[57] ABSTRACT

A scanned volume computerized tomography scanner in which an electron beam is scanned along a target to generate successive cones of x-rays. A vane collimator receives said x-rays and from successive adjacent fan becomes for irradiating a volume of an object. A detector array receives the x-ray fan becomes and generates signals representative of the transmitted x-ray amplitude across the fan beams. The object and x-ray source are rotated relative to one another to collect data for reconstructing an image of the scanned volume.

7 Claims, 5 Drawing Sheets

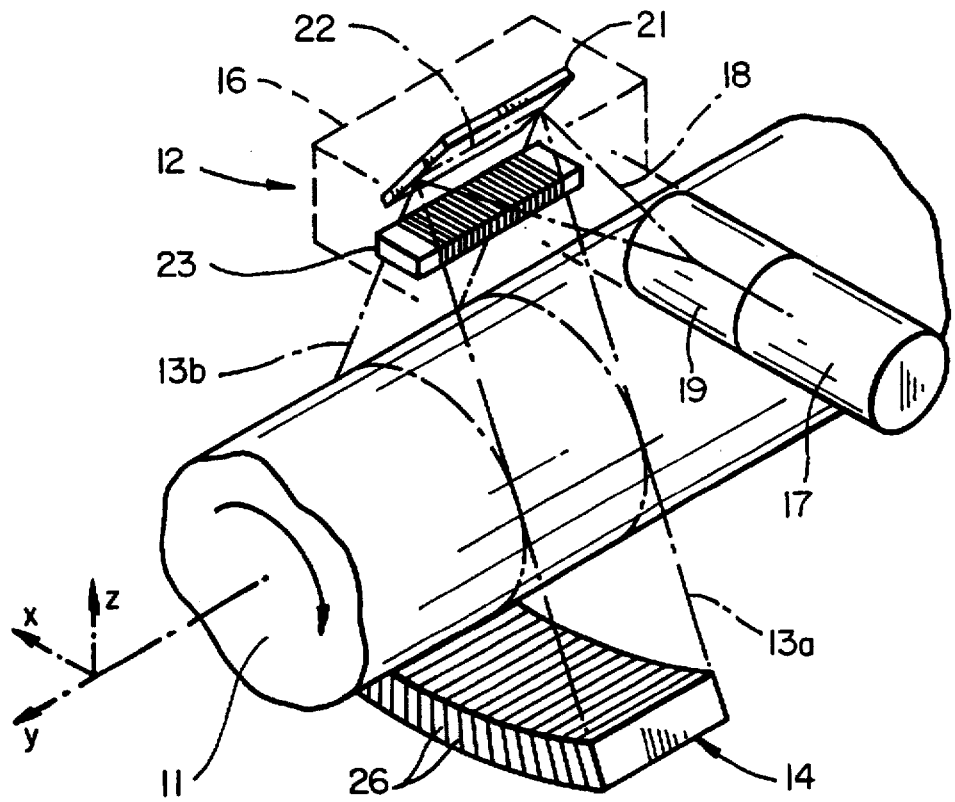
FIG_1
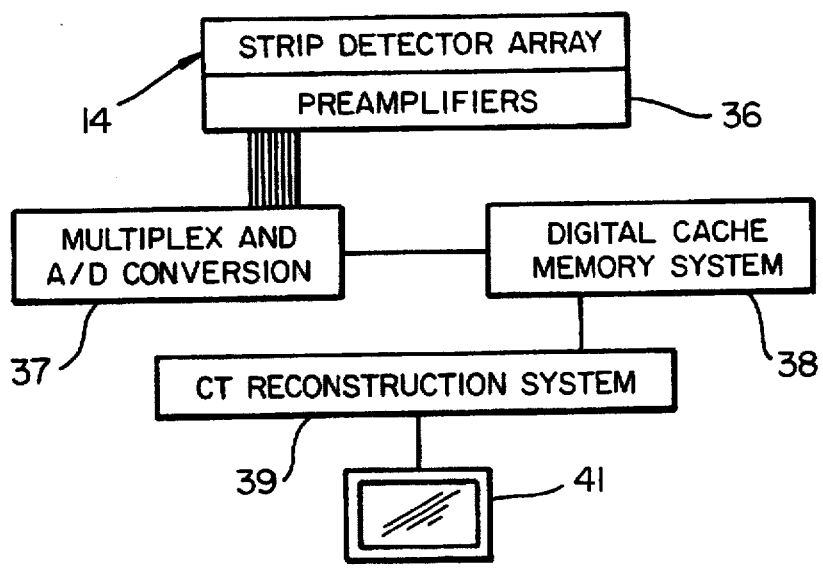
FIG_2

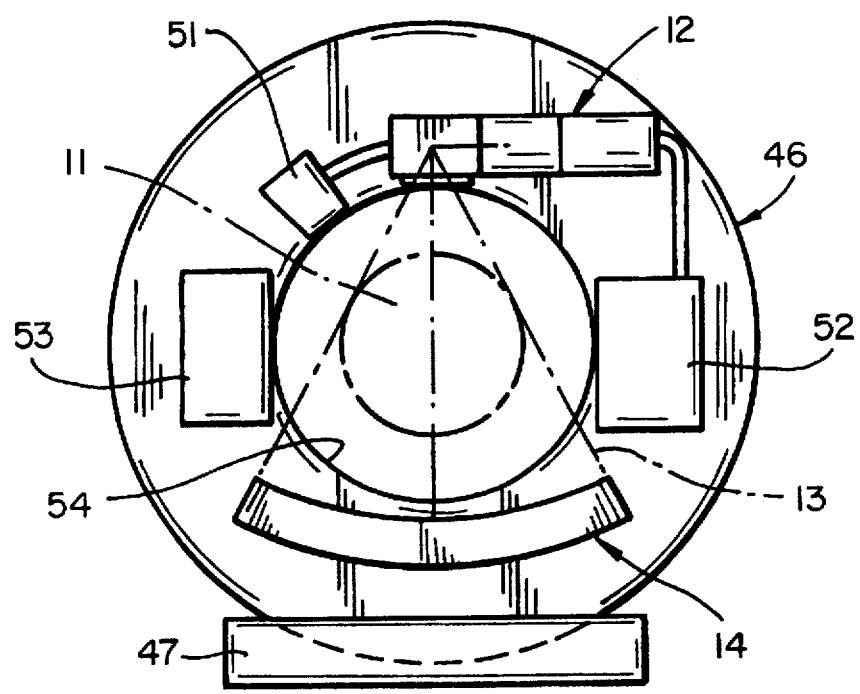
FIG_3
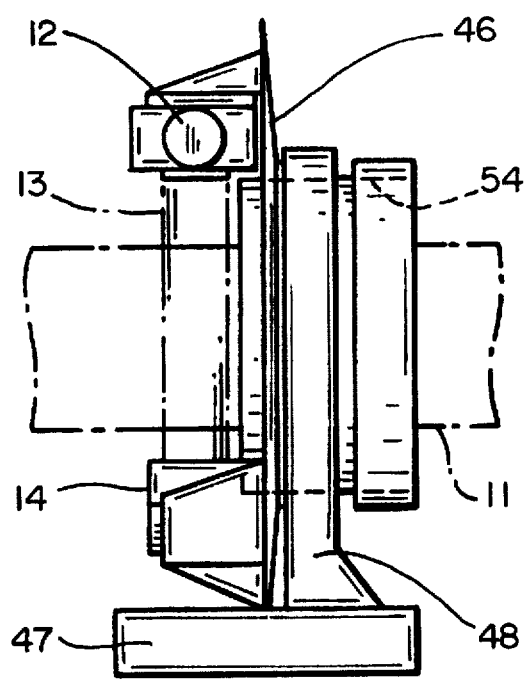
FIG_4

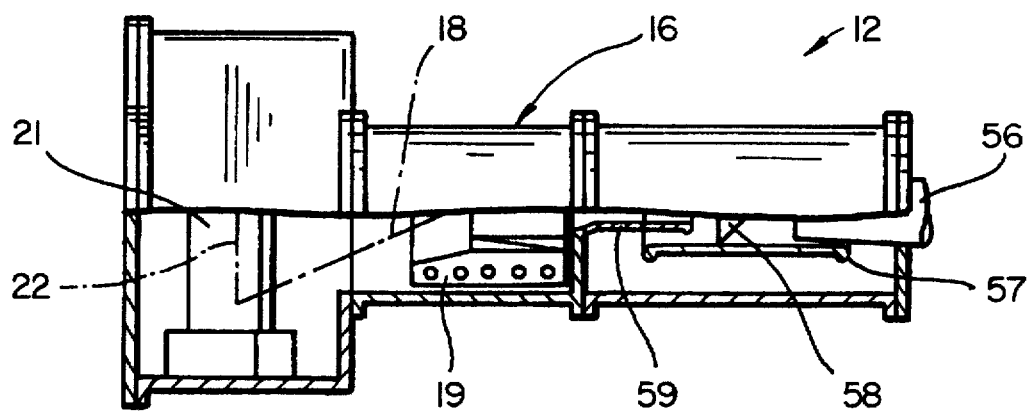
FIG_5
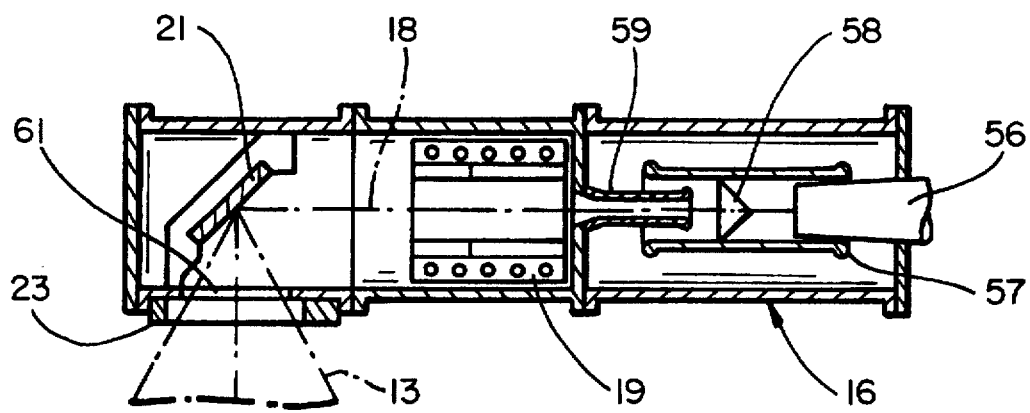
FIG_6
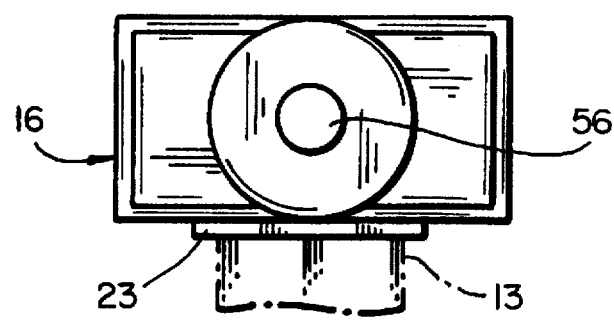
FIG_7

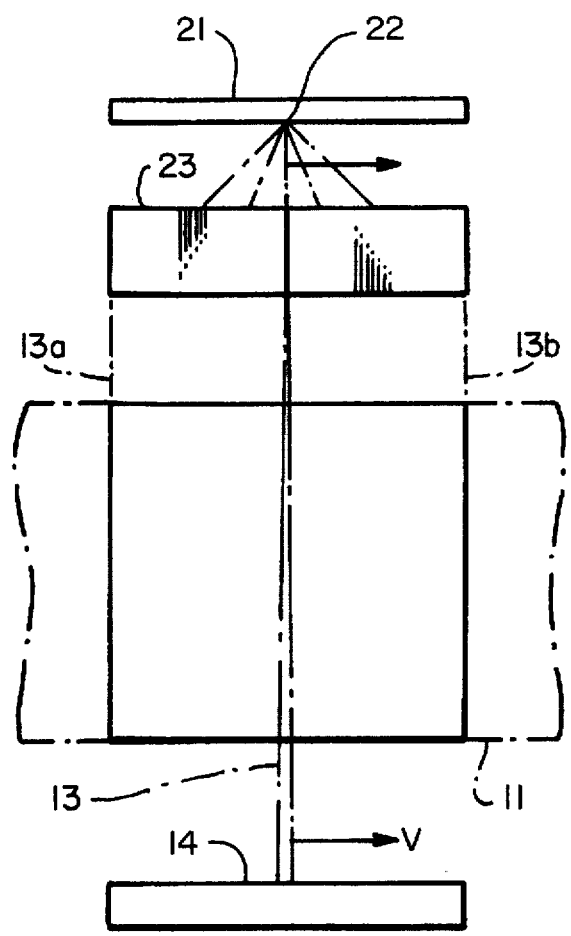
FIG_8
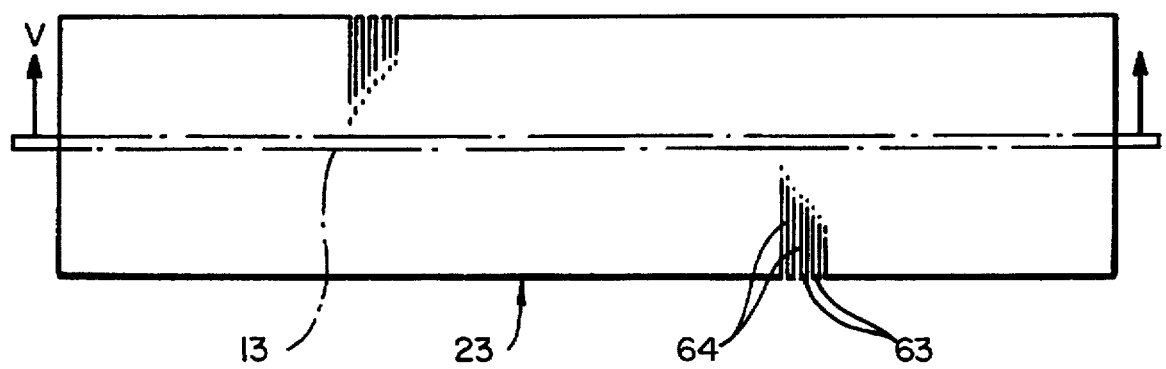
FIG_9

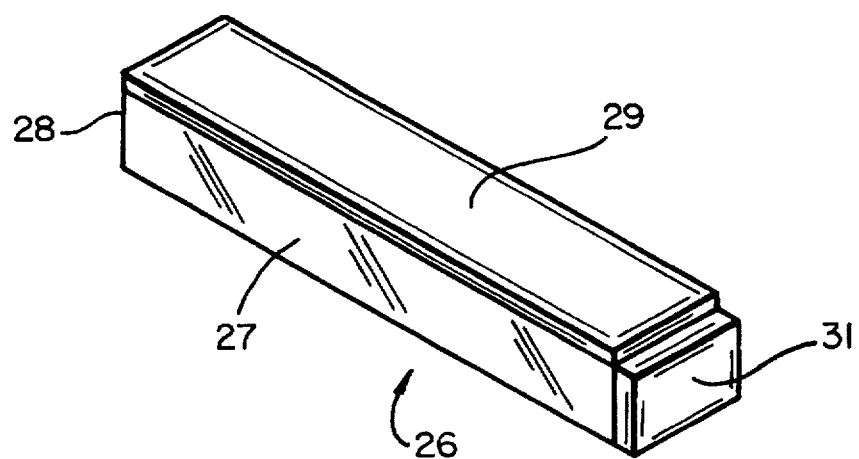
FIG_10
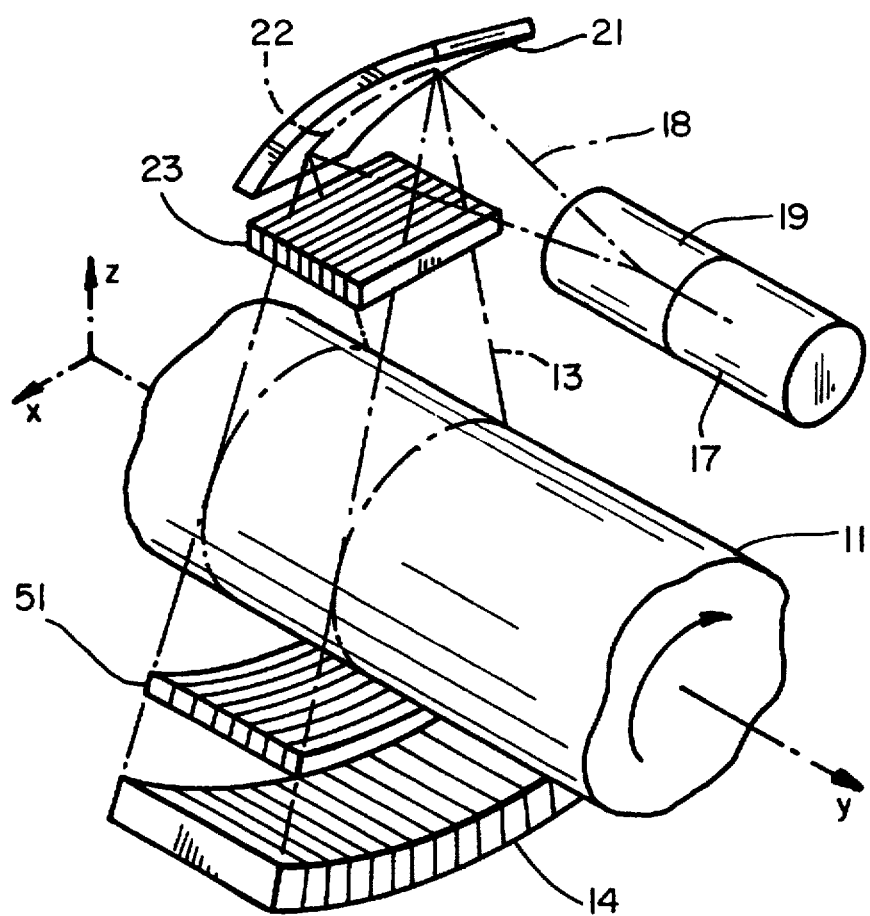
FIG_11 ns. 5,712,889

SCANNED VOLUME CT SCANNER

This is a continuation of application Ser. No. 08/675,420 filed 3 Jul. 1996, now abandoned, which is a continuation of prior application Ser. No. 08/294,964, filed 24 Aug. 1994, now abandoned.

BRIEF DESCRIPTION OF THE INVENTION

This invention relates generally to computerized-tomography (CT) scanners, and more particularly to scanned volume CT scanners.

BACKGROUND OF THE INVENTION

CT scanners have become the preferred equipment for imaging the interior of objects using x-rays. CT scanners are widely applied in medical imaging and are becoming increasingly accepted for a variety of industrial inspection applications.

The main advantage of CT over previous x-ray imaging methods is the ability to image a thin slice of an object, thus avoiding the problem of superposition of overlying and underlying structures in the image. A series of thin slices scanned sequentially forms a volume image. Such a three-dimensional volume image can be displayed with modern work stations using a wide range of surface and volume rendering techniques.

A limitation of most CT scanners has been the relatively long time needed for acquisition of the data needed to reconstruct a volume image. Since most machines scan one slice at a time using 360° rotation of a source and detector around the object, a large number of such mechanical rotations, up to 100 or more is needed. This can require minutes of scan time at a rotation of one revolution per second.

Two developments have improved the speed of volume data acquisition. One method uses an x-ray tube producing a cone of x-ray that is detected opposite the scanned object using an area detector array. Typically the area detector is a fluorescent screen. The light from the fluorescent screen is amplified by an image intensifier and projected onto the CCD detector of a video camera. The video signal is then digitized to acquire the area x-ray projection data. This system is rotated around the object only once to obtain the volume data. This type of system is referred to as a cone beam CT scanner. There are two problems that limit the image quality of this type of system. The first is that no suitable mathematical algorithm for reconstructing the data obtained in the cone beam geometry exists. This leads to image degradation due to "cone beam artifact." A second limitation is that the characteristics of the area detector fall short of the requirements for a high-resolution CT system.

A second approach to high-speed volume imaging is the use of electron-beam scanning as incorporated in the Ultrafast CT scanner described generally in U.S. Pat. No. 4,352,021. This scanner can obtain cross section data at a speed of up to 17 slices per second. The x-ray scan is performed by magnetically sweeping an electron beam along a curved anode target ring surrounding the scanned object. One advantage of this system is that the rapid scan speed can freeze the motion of moving organs in the human body and produce sharp images. Electron-beam scanners are large, complex, and costly. There is a need for a fast, small, simple, inexpensive volume scanner.

OBJECTS AND SUMMARY OF THE INVENTION

It is an object of this invention to provide an improved volume CT scanner.

It is another object of the invention to provide a fast, simple, inexpensive volume CT scanner.

The foregoing and other objects of the invention are achieved by a volume CT scanner for scanning a volume of an object which includes means for generating an electron beam and linearly scanning it along a target to form a succession of cone-shaped x-ray beams. A vane collimator receives said successive cone-shaped x-ray beams and forms a succession of adjacent parallel fan-shaped x-ray beams which irradiate a volume of the object. The x-rays transmitted through the object are detected by a detector which provides output data signals representative of the amplitude of said transmitted x-ray beams at a plurality of fan angles for each of said fan beams.

BRIEF DESCRIPTION OF THE DRAWINGS

The foregoing and other objects of the invention will be more clearly understood from the following detailed description when read in conjunction with the accompanying figures of which:

FIG. 1 is a schematic isometric view of a scanned volume CT scanner in accordance with the invention;

FIG. 2 is a block diagram of the signal processing system and display;

FIG. 3 is a front elevational view of a scanner incorporating the elements of FIG. 1;

FIG. 4 is a side elevational view of the scanner shown in FIG. 2;

FIG. 5 is a top plan view of the electron gun, target and collimator of the volume CT scanner;

FIG. 6 is a side elevational view of FIG. 4;

FIG. 7 is a rear elevational view of FIG. 4;

FIG. 8 is a schematic side elevational view showing the formation of the fan beams and their detection;

FIG. 9 is a top plan view of a vane collimator;

FIG. 10 shows a suitable x-ray detector element used in the detector array of FIG. 8; and FIG. 11 is a schematic view of another embodiment of the invention.

DESCRIPTION OF PREFERRED EMBODIMENT(S)

Reference is first made to the schematic illustration of FIG. 1. An object 11 to be scanned; for example, the human body, is placed between a source 12 of adjacent parallel x-ray fan beams 13 and a detector assembly 14. The x-ray source is disposed in an evacuated envelope 16 which includes an electron gun assembly 17 which generates an electron beam 18. The electron beam 18 is deflected by a magnetic deflector assembly 19. A target 21 is placed in the evacuated envelope to receive the electron beam and generate cones of x-rays responsive to the incident electron beam. The beam is linearly scanned across target 21 along the line 22 whereby a plurality of successive cone beams are generated. A vane collimator 23 which includes a plurality of spaced parallel vanes forming a plurality of slots is placed opposite the target 21 and serves to pass only a thin fan beam of x-rays as the electron beam strikes the target opposite a slot between adjacent vanes. As the beam scans across the target opposite collimator slots successive adjacent fan beams are formed. The plurality of spaced adjacent fan beams traverse the volume of the object under examination as shown between the fan beams 13a and 13b of FIG. 1.

The detector 14, FIGS. 1, 8 and 9, receives the x-rays after they traverse the object. The detector 14 comprises a linear array of elongated detector elements 26. Each detector includes a transparent light guide 27 which may be made of clear plastic material with polished surface 28, preferably including an external reflective coating (not shown). The upper wall of the light guide is provided with a layer of scintillation material 29 such as $CdWO_4$ or a ceramic scintillator. The scintillator converts incoming x-rays into light. The light produced by the scintillation material is collected in the light guide and transmitted to one end of the light guide by multiple reflections from the walls of the light guide and the other end of the light guide. A photodiode 31 is placed at the one end of the light guide. Since the maximum size of the photodiode will be limited to something like one or two centimeters, some type of minifying techniques may be used to collect the light from the end of the light guide for the smaller photodiodes. One particular method is described in U.S. Pat. No. 4,535,243. Other methods of receiving the light from the ends of the light guides might be the use of fiber optics to convey the light from the light guides to the photodiode, or to condense the light with a cylindrical lens. The light guide photodiode combination provides a signal which is representative of a particular pencil like portion of each fan beam 13 at a plurality of fan angles whereby a plurality of signals are generated for each slice of the object traversed by the fan beam. The detector output is therefore a plurality of signals representative of the object for each position across the fan beam for each position of the fan beam throughout the scanned volume.

In order to provide a CT image of the volume being scanned the object and x-ray source are rotated relative to one another whereby the plurality of scanned fan beams impinge upon the target at a plurality of positions of the beam over a 360° rotation of the x-rays with respect to the object. The output from each of the detector elements 26 of the detector array 14 is amplified by a preamplifier 36, FIG. 2. The output is multiplexed and digitized by the multiplexer and A to D converter 37. Sufficient data for reconstruction can be obtained by rotation through 180° plus the fan beam angle. The digitized signals are stored in digital memory cache 38 during acquisition. The stored digitized signals are conventionally processed in a reconstruction system 39 and applied to display 41 which displays a 3-D image of the interior of the object being scanned.

Referring more particularly to FIGS. 3 and 4, a gantry 46 is rotatably supported on a base 47 by upwardly extending support 48. Suitable means (not shown) are provided for rotating or oscillating the gantry. The rotation or oscillation may be continuous or stepped. The x-ray source 12 is mounted on the gantry. The target 21 is cooled by a refrigerant from refrigeration means 51 mounted on the gantry. A high-voltage power supply 52 provides power to the electron gun which generates the electron beam. The detector assembly 14 is mounted on the gantry opposite the source 12. A computer or data processor 53 is included for preprocessing (preamplifiying, multiplexing and digitizing) the data from the detectors and for controlling deflection of the electron beam. An object 11 is suitably mounted within the opening 54 formed in the gantry. For example, the object to be scanned can be presented to the gantry by suitable conveyor means or a patient table (not shown).

The x-ray source 12 is shown in more detail in FIGS. 5, 6, and 7. A suitable electron gun is described in U.S. Pat. No. 4,621,213 dated Nov. 4, 1986 and the disclosure of said patent is incorporated herein by reference. The electron gun includes a cathode assembly 56 which serves as a source of electrons, a focusing electrode 57 and a Pierce electrode 58. An anode 59 provided the accelerating voltage and together with the Pierce electrode and the focusing electrode forms an electron beam which travels through magnetic deflection means 19. The deflection means 19 sweeps the electron beam linearly along the target 21. As described the target 21 is cooled by circulating refrigerant therethrough. As previously described the electron beam 18 forms a cone of radiation which is intercepted by the vane-type collimator 23 to form successive fan-shaped beams 13 parallel and adjacent to each other. The evacuated envelope 12 includes a window 61 which passes the x-rays to the collimator 23. An electron beam of 140–200 kV can be produced using the modified Pierce-diode electron gun described above. The target may be of any length; for example, 200 mm or longer. The focal spot size is preferably elongated in such a manner as to produce the maximum focal area with minimum resolution degradation in the image. Focal spot shape is controlled with the quadrupole magnetic deflection means 19 of a type more completely described in U.S. Pat. No. 4,644,168. The target surface shown is a flat surface positioned parallel to the axis of rotation of the gantry.

As described, the x-ray cone emitted by the target is collimated into a flat, thin fan beam for each target position. This is done by using a vane collimator 23 placed between the x-ray source and the scanned object. Referring to FIG. 9, the collimator includes vanes 63, typically thin sheets of tantalum or other high atomic number material, separated by a small space or gap 64. The aspect ratio is the length of the vanes 63 in the direction of the x-rays to the with of the spacing 64 and must be typically 200:1. The thickness of the sheets is typically 0.1 mm. The fan beam collimation can be additionally enhanced by use of an additional collimator placed between the object and the detector array. This added detector collimator can have openings corresponding to each slice. The openings can be substantially less than the slice spacing in order to enhance z-axis resolution.

The electrical signals from the photodiodes 31 record the light intensity of each detector element disposed at different fan beam angles as a function of time. Since the x-ray beam will scan across the detector width repetitively during angular rotation time encodes z-position along the width as well as rotational angle. In order to acquire data for 40 slices the detector signal must be sampled 40 times for each position. Thus, the sampling speed is approximately 20 microseconds per detector. This gives a data rate of 50 thousand samples per second per detector or 50 million samples per second for a system of 1,000 detector. This process of converting the analog photodiode signal into digital values requires a high-speed digital-to-analog conversion system 37, FIG. 2, such as that currently employed in the Iraalton Ultrafast CT scanner. Since the volume scanner acquires data at a rate substantially faster than most CT scanners, it is desirable to have a fast reconstruction system 39. This requires a parallel array of image reconstruction processors, each employing the most efficient algorithms available in medical CT scanners.

As described, the entire assembly of detector electronics, electron beam x-ray source is mounted on a rotating gantry in order to provide a 360° rotation. In the case of a rotating gantry a system is needed to supply high-voltage to the electron beam source and for extracting signal data from the processors. A preferred method is to use slip rings. However, a variety of alternatives are possible. The gantry may be oscillated and the power and signals can be transmitted through cables that wind up during scanning and unwind during a scan in the opposite direction. If slip rings are used they may be either of high-voltage type or low-voltage type. Low-voltage slip rings are simpler but require a compact high-voltage generator to be included on the rotating scanner. The data signals can be transmitted either through a series of low-voltage slip rings or by other electronic means such as infrared and r.f. transmission.

As an alternative the gantry may be stationary eliminating the need for slip rings. However, this adds complications to handling objects. If the objects are continuously feed from a conveyor belt then a mechanism that transfers the objects to a rotation device is required. Since the rotating speed is relatively high additional devices to restrain the objects and their content during rotation may be required.

Scanning of the target in the y-z plane, FIG. 1, may introduce undesirable shifts in electron beam angle across the length of the scan volume and a shift in x-ray intensity and voltage across the fan. An alternative design is schematically shown in FIG. 4 where like reference numbers have been applied to parts already described. An additional collimator 51 is shown between the object 11 and the detector array 14. The target 21 is curved in such a way as to maintain a constant angle of the electron beam with respect to the target as the target is scanned in the z-x plane. The second advantage of the curved target concept is the energy distribution in the fan is more homogeneous since the central ray of the x-ray fan can be perpendicular to the surface of the target in the plane of the fan. A third advantage is that the target can be placed at an angle in the y-z plane such that the focal spot can be elongated as in conventional x-ray tubes.

Thus, there has been provided a fast, simple, inexpensive volume CT scanner.

What is claimed is:

1. A volume CT scanner for scanning an object including:
   a target;
   means for generating an electron beam and linearly scanning the beam along said target to form a succession of cone-shaped x-ray beams;
   a vane collimator disposed to receive said successive cone-shaped x-ray beams and form a succession of adjacent parallel fan-shaped x-ray beams which successively irradiate adjacent planar slices along the length of a volume of said object to be Scanned; and a single detector array extending along said length comprising a plurality of adjacent longitudinally elongated detector elements extending across each of said beams for receiving said receiving said succession of transmitted parallel fan-shaped x-ray beams and successively generating data signals representative of the amplitude of each of said transmitted parallel fan-shaped x-ray beams across each of said beams as they are transmitted through and along said volume, each of said longitudinally elongated detector elements being arranged to successively receive said plurality of said transmitted x-ray beams representing a plurality of planar slices in said volume.

2. A volume CT scanner for scanning a volume of an object comprising:
   means for generating and linearly scanning an electron beam;
   a target for receiving said electron beam whereby, as the beam is scanned linearly along said target, successive cones of x-rays are generated;
   a vane collimator including a plurality of spaced vanes defining slots disposed to receive said cones of x-rays and form a succession of thin-spaced, fan-shaped x-ray beams, one for each of said cones as they are opposite a slot to scan said fan-shaped beams linearly along the length of the volume of said object to be scanned;
   means for providing relative rotation between said fan beams and said object;
   a single array elongated detector elements extending along the length of the volume to be scanned for receiving said fan-shaped x-ray beams transmitted through said object and generating a succession of data signals representative of the x-ray transmission through said object across each of said beams, along said length for each of said fan-shaped x-ray beams; and
   means for processing said signals to provide an image of the volume of said object.

3. A volume CT scanner for scanning objects comprising:
   means for generating an electron beam;
   a target for receiving said electron beam and generating a cone of x-rays;
   means for deflecting said electron beam so that it scans linearly along said target to form successive cones of x-rays;
   a collimator disposed opposite said target to receive said cones of x-rays, said collimator comprising a plurality of parallel spaced vanes forming a plurality of slots, each of said slots receiving said x-rays and forming a fan-shaped x-ray beam, whereby a plurality of parallel spaced fan beams are successively formed along the length of the volume of said objects to be scanned; and
   a detector assembly comprising of a single array extending across each of said fan-shaped beams and extending over said length of adjacent elongated detector elements for receiving said succession of transmitted fan-shaped beams and generating successive signals representative of x-ray intensity angularly across each of said beams.

4. A volume CT scanner as in claim 3 including a second collimator having spaced vanes forming a plurality of slots disposed adjacent said detector assembly to further collimate said fan-shaped beam.

5. A volume scanner as in claim 3 including means for providing relative rotation between the x-ray source and detectors and the object.

6. A volume scanner as in claim 5 wherein the target is a flat target scanned in a plane which is parallel to the axis of rotation.

7. A volume scanner as in claim 5 wherein the target is a curved target scanned in a plane which includes the axis of rotation.

* * * * *